United States Patent [19]

Kaiser

[11] 4,203,900
[45] May 20, 1980

[54] PROCESS FOR PREPARING 2-OXAZOLINES

[75] Inventor: Mark E. Kaiser, Midland, Mich.

[73] Assignee: The Dow Chemical Company, Midland, Mich.

[21] Appl. No.: 756,146

[22] Filed: Jan. 3, 1977

[51] Int. Cl.$^2$ .................. C07D 263/12; C07D 263/14
[52] U.S. Cl. .................................................. 548/239
[58] Field of Search .................................... 260/307 F

[56] References Cited

U.S. PATENT DOCUMENTS 2,844,589  7/1958  Hess ..................................... 260/307

FOREIGN PATENT DOCUMENTS 2512201  9/1975  Fed. Rep. of Germany.

Primary Examiner—Mark L. Berch

Attorney, Agent, or Firm—L. Wayne White; Michael L. Glenn

[57] ABSTRACT

A cyclodehydration reaction is described for preparing 2-oxazolines which comprises reacting in liquid phase (a) an N-(2-hydroxyalkyl)carboxamide with (b) a small but catalytic amount of an iron-containing compound. The reaction is normally conducted at elevated temperatures (e.g., 180°–200° C.) and under reduced pressure. Both 2-H- and 2-substituted-2-oxazolines are prepared by this process. For example, 2-H-2-oxazoline and 2-ethyl-2-oxazoline were prepared in 83.1 percent and 90.2 percent yields, respectively, by contacting the appropriate N-(2-hydroxyethyl)carboxamide with ferrous chloride tetrahydrate at temperatures of approximately 180°–200° C./50 mm Hg. Under these conditions, the oxazoline product and water were codistilled from the reaction mixture essentially as fast as they were formed.

12 Claims, No Drawings

PROCESS FOR PREPARING 2-OXAZOLINES

BACKGROUND OF THE INVENTION

1. Field of the Invention

This invention pertains to a novel cyclodehydration reaction which produces 2-oxazolines using iron-containing compounds as the catalyst.

2. Description of the Prior Art

The 2-oxazolines are a known class of compounds whose chemistry has been summarized by Wiley et al., *Chemical Reviews*, Vol. 44, 447–476 (1949); Seeliger et al., *Angew. Chem. International Edition*, Vol. 5, No. 10, 875–888 (1966), and Frump, *Chemical Reviews*, 1971, Vol. 71, No. 5, 483–505. Patents and other references pertaining to monomeric 2-oxazolines have normally been classified by the U.S. Patent and Trademark Office under the classification 260/307F.

The 2-oxazolines correspond to the general formula

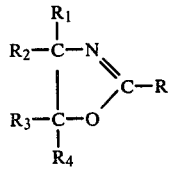

I.

wherein R is hydrogen, hydrocarbyl or inertly-substituted hydrocarbyl, and $R_1$–$R_4$ are each independently hydrogen, hydrocarbyl, or an inertly-substituted hydrocarbyl group. The best known oxazolines are those in which R is hydrogen, alkyl or phenyl and $R_1$ and $R_2$ are hydrogen, lower alkyl or hydroxymethyl or derivatives thereof (e.g., esters) and $R^3$ and $R_4$ are each hydrogen.

2-H-2-Oxazoline is the first member of the oxazoline series and is the "simplest" molecule. It corresponds to formula II.

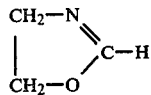

II.

The 2-H2-oxazolins and particularly II above are generally quite different from the corresponding 2-substituted-2-oxazolines. This is illustrated by the fact that many conventional processes for preparing 2-substituted-2-oxazolines are not particularly satisfactory for the preparation of the corresponding 2-H2-oxazolines. For example, many 2-substituted-2-oxazolines are conventionally prepared by dehydrochlorinating an N-(β-chloroalkyl)carboxamide with aqueous alkali. Compound II, on the other hand, is produced by this process in only very low yields and is accompanied by decomposition of the desired product. H. Wenker, *J. Am. Chem. Soc.*, 60, 2152 (1938).

Another common technique for preparing 2-oxazolines is the cyclodehydration of N-(β-hydroxyalkyl)carboxamides over various catalysts. Litt et al. (U.S. Pat. No. 3,681,329 and U.S. Pat. No. 3,681,333) claimed that 2-H-2-oxazolines could be prepared by contacting the appropriate formamides with compounds of manganese, cobalt, molybdenum, tungsten and the rare earth metals. Unfortunately, there is no experimental data in Litt et al. which would substantiate this allegation. Hess teaches in Canadian Pat. No. 536,594 and British Pat. No. 758,972 that II can be prepared by a cyclodehydration of N-(2-hydroxyethyl)formamide in the presence of a dehydrating agent (specifically diatomaceous earth, sulfuric acid, aluminum oxide and iron oxide). The yields reported by Hess were higher than the yield reported by Wenker but were still rather low and commercially unsatisfactory. In contrast to this, Litt et al. teach in U.S. Pat. No. 3,562,263 that 2-substituted-2-oxazolines are prepared in excellent yield by cyclodehydration of N-(2-hydroxyalkyl)carboxamides over aluminum oxide.

In view of these differences between 2-H2-oxazolines and 2-substituted-2-oxazolines in the various methods of preparation, it was surprising to find a class of compounds which would catalyze the cyclodehydration of N-(2-hydroxyethyl)formamides and carboxamides to form the corresponding 2-H2-oxazolines or the 2-substituted-2-oxazolines.

SUMMARY OF THE INVENTION

A novel cyclodehydration process has been discovered for preparing 2-oxazolines. The novel process comprises reacting by contacting in liquid phase (a) an N-(2-hydroxyalkyl)carboxamide with (b) a small but catalytic amount of an iron-containing compound.

The discovery that iron-containing compounds would catalyze the instant cyclodehydration reaction was most surprising for reasons set forth above and particularly in view of the teaching by Litt et al. in U.S. Pat. Nos. 3,681,329 and 3,681,333 that iron compounds are inferior catalysts in this reaction.

DETAILED DESCRIPTION OF THE INVENTION

The N-(2-hydroxyalkyl)carboxamides used in the instant process are a known class of compounds which can be represented by the formula

III.

wherein R and $R_1$–$R_4$ are each independently hydrogen, hydrocarbyl or inertly-substituted hydrocarbyl groups. By "inert" is meant that the substituents are inert in the instant process. Preferred reactants are those wherein R is hydrogen, alkyl of from 1 to about 17 carbon atoms or phenyl and $R_1$ and $R_2$ are hydrogen, lower alkyl ($C_1$–$C_6$), hydroxymethyl or alkanoyloxymethyl groups (alkyl—C(O)—OCH2—) of up to about 17 carbon atoms and $R_3$ and $R_4$ are hydrogen. Most preferred reactants are those wherein R is hydrogen, methyl, ethyl or phenyl, and $R_1$–$R_4$ are each hydrogen. These preferences are based upon the commercial availability of the ethanolamines which are used in preparing such carboxamides.

The N-(2-hydroxyalkyl)carboxamides are conveniently and typically prepared by reacting a carboxylic acid or a lower alkyl ester of a carboxylic acid with an ethanolamine of the formula

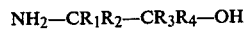

IV.

wherein $R_1$–$R_4$ have the aforesaid meaning.

The carboxylic acid/amine salt which is formed initially in these reactions can be used in the instant process in place of the carboxamide. When such carboxylic acid/amine salts are used, the carboxamide is generated in situ.

Examples of suitable N-(2-hydroxyalkyl)carboxamides include those of formula III wherein R and $R_1$–$R_4$ have the values set forth in Table I below.

TABLE I

| R | $R_1$ | $R_2$ | $R_3$ | $R_4$ |
|---|---|---|---|---|
| $CH_3$ | H | H | H | H |
| $CH_3$ | $C_4H_9$ | H | H | H |
| $CH_3$ | $C_2H_5$ | $C_2H_5$ | H | H |
| $C_2H_5$ | H | H | H | H |
| $C_2H_5$ | $CH_2OH$ | $CH_2OH$ | H | H |
| $C_2H_5$ | $CH_2O(O)C-C_{17}H_{35}$ | H | H | H |
| $C_3H_7$ | $C_6H_5$ | H | $C_6H_5$ | H |
| $C_7H_{15}$ | $CH_3$ | H | H | H |
| $C_9H_{19}$ | $CH_3$ | $CH_3$ | H | H |
| $C_{11}H_{23}$ | $CH_3$ | H | $CH_3$ | H |
| $C_{17}H_{35}$ | H | H | H | H |
| $C_6H_5$ | H | H | H | H |
| $C_6H_4CH_3$ | $C_6H_5$ | H | $CH_3$ | H |
| $C_6H_5CH_2$ | H | H | $CH_3$ | $CH_3$ |
| $CH_3(CH_2)_7CH=CH(CH_2)_7$ | H | H | H | H |
| cyclohexyl | H | H | H | H, | and other like compounds.

The compounds in Table I do not represent an all inclusive listing of suitable carboxamide reactants, obviously, and other compounds falling within formula III are similarly useful.

The catalysts in the instant cyclodehydration reaction are iron-containing compounds. Suitable catalysts are inorganic and organometallic iron compounds which are soluble in the carboxamide reactant or liquid reaction medium. The term "soluble" means that the iron-containing compound has at least a minimum solubility (e.g., about 100 parts per million or more) at the reaction temperature. Examples of suitable iron-containing compounds which can be used as catalysts include: ferrous chloride, ferric chloride, ferric bromide, ferric iodide, ferrous sulfate, ferric sulfate, ferric ammonium sulfate, ferric potassium sulfate, ferric octoate, iron pentacarbonyl, ferric acetate, ferric acetylacetonate, ferric ammonium oxalate, ferric benzoate, ferric citrate, ferric naphthenate, ferric phosphate, ferrous acetate, and the like. The inorganic iron compounds are preferred and the iron chlorides, bromides and iodides are more preferred. Ferrous and ferric chlorides and sulfates ae the most preferred catalysts.

The iron-containing compounds are used in the instant process is small but catayctic amounts. Normally the iron-containing compounds are added in amounts of from about 0.005 to about 0.4 mole of iron-containing compounds per mole of carboxamide reactant but more or less of the iron-containing compound can be used, if desired.

The instant cyclodehydration reaction may be conducted neat or in solution with a suitable inert solvent. By "inert" is again meant inert in the process. Suitable such inert solvents include, for example, chlorinated hydrocarbon solvents, aromatic hydrocarbon solvents, cycloaliphatic hydrocarbon solvents, aliphatic hydrocarbon solvents, and the like. It is preferred, however, to conduct the reaction without any solvent added (i.e., neat).

The reaction temperature must, obviously, be sufficient to promote the cyclodehyration reaction and is normally selected in the range of from about 140° C. to about 280° C. Preferred reaction rates have been observed at temperatures of from about 160° C. to about 250° C.

The instant cyclodehydration reaction is also preferably conducted under reduced pressure. By conducting the reaction in this manner, product recovery is facilitated in that frequently a reaction temperature may be chosen which is above the boiling point of the 2-oxazoline product and below the boiling point of the N-(2-hydroxyalkyl)carboxamide reactant. In this manner, the 2-oxazoline can be removed from the reaction mixture as a volatile gas essentially as fast as it is formed. This is very desirable since the instant cyclodehydration reaction is a reversible process and by removing the products, the reaction is forced to completion by substantially reducing the reverse reaction. Water normally codistills with the 2-oxazoline product.

The instant process may be conducted in a batch process or in a continuous manner. In the preferred continuous process, of course, the N-(2-hydroxyalkyl)-carboxamide reactant is metered into the reaction vessel at essentially the same rate as the 2-oxazoline and water are removed overhead as volatile gases.

EXPERIMENTAL

The following examples will further illustrate the invention:

EXAMPLE 1

Preparation of 2-H-2-Oxazoline

N-(2-Hydroxyethyl)formamide (100.2 g/1.125 mole) and ferrous chloride tetrahydrate (1.58 g; 0.008 mole) was added to a reaction vessel equipped with a stirring means, heating means, and a distillation means comprising a distillation column with a takeoff head and receiver, and a vacuum source. The pressure over the reaction mixture was adjusted to 50 mm Hg and the temperature raised to 180°–187° C. The head temperature of the distillate was between about 37° C. and about 42° C. The material collected from the overhead distillate was a water white liquid weighing 89.5 g. Analysis of this water white liquid using gas chromatography indicated that it was 79.2 weight percent oxazoline and a Karl Fischer analysis indicated that the material was 19.9 weight percent water. The yield derived from this analytical data indicated that 2-H-2-oxazoline was produced in 88.7 percent of theoretical yield, based on the N-(2-hydroxyethyl)formamide charged to the reaction vessel.

The 2-H-2oxazoline can be recovered from the aqueous distillate, if desired, by solvent extraction using chloroform or other inert water immiscible organic solvents.

EXAMPLE 2

2-H-2-Oxazoline was prepared in approximately 84 percent yield following the procedure of Example 1 except using $FeSO_4.7H_2O$ as the catalyst.

EXAMPLE 3

In like manner, 2-H-2-oxazoline was prepared in approximately 82 percent yield using hydrated ferric sulfate in place of ferrous chloride as the catalyst.

By way of comparison, it is noted that Hess, supra, produced 2-H-2-oxazoline in extremely low yields using ferric oxide as the catalyst. We observed similar poor yields in experiments using ferric hydroxide and ferrous gluconate as catalysts in attempts to prepare 2-H-2-oxazoline; these iron compounds were insoluble in the N-(2-hydroxyethyl)formamide reactant under conditions set forth in the above examples.

EXAMPLE 4

Using the apparatus described in Example 1, an aliquot of N-(2-hydroxyethyl)propionamide amounting to approximately 0.3 mole and ferric chloride (about 0.5 mole) were charged to the reaction vessel and the pressure reduced to 120 mm Hg. The reaction mixture was then heated to approximately 200° C. and held at this reaction temperature until material began to distill overhead. At this point, additional N-(2-hydroxyethyl)propionamide was added dropwise at approximately 1.4 g/minute. During this addition, the pot temperature was maintained at approximately 200° C. and the water white distillate came overhead at a temperature of from 65° C. to about 72° C. After the addition was complete, the pot temperature was raised to approximately 250° C. to drive off residual amounts of the 2-ethyl-2-oxazoline. The distillation head temperature reached a maximum of 90° C. in this postheating period. The distillate was a water white liquid upon cooling which was analyzed by gas chromatography and Karl Fischer titration. This analytical data showed that 2-ethyl-2-oxazoline was thus produced in 90 percent yield, based upon the amount of N-(2-hydroxyethyl)propionamide charged to the reaction vessel.

EXAMPLE 5

Using the procedure set forth in Example 4, 2-ethyl-2-oxazoline was produced in 90.2 percent yield using ferrous chloride tetrahydrate in place of the ferric chloride catalysts.

EXAMPLE 6

2-Ethyl-2-oxazoline was produced in approximately 76 percent yield in a batch process by warming the salt of propionic acid and ethanolamine over ferrous chloride tetrahydrate (approximately 2 mole percent to approximately 200° C./50 mm Hg. There was a pause in the rise in temperature during which the acid/amine salt was converted to the amide. Otherwise, the reaction proceeded essentially the same as Example 5 above. The product was similarly recovered as an overhead distillate with water.

EXAMPLE 7

In a similar batch process, 2-ethyl-5-methyl-2-oxazoline was produced in approximately 84 percent yield by cyclodehydrating N-(2-hydroxypropyl)propionamide over ferrous chloride tetrahydrate. The reaction proceeded very rapidly under somewhat milder conditions (165° C.).

Other oxazolines can be similarly prepared using the iron compounds set forth in Examples 1-7 above or other soluble iron compounds as catalysts.

What is claimed is:

1. A cyclodehydration process for preparing a 2-oxazoline comprising reacting by contacting in liquid phase (a) an N-(2-hydroxyalkyl)or N-(inertly-substituted 2-hydroxyalkyl) carboxamide or a carboxylic acid/amine salt precursor of said carboxamides with (b) a small but catalytic amount of a soluble inorganic iron-containing compound, said iron-containing compound not being an iron oxide.

2. The process defined by claim 1 wherein said N-carboxamide corresponds to the formula

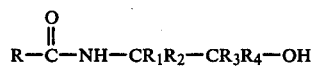

where R is hydrogen, alkyl or phenyl, $R_1$ and $R_2$ are each independently hydrogen, lower alkyl, hydroxymethyl or alkanoyloxymethyl groups of up to about 17 carbon atoms, and $R_3$ and $R_4$ are each hydrogen.

3. The process defined by claim 2 wherein R is hydrogen, alkyl of from 1 to about 17 carbon atoms or phenyl, and $R_1$-$R_4$ are each hydrogen.

4. The process defined by claim 3 wherein R is methyl or ethyl.

5. The process defined by claim 1 wherein said catalyst is charged in amounts of from about 0.005 to about 0.4 mole of iron-containing compound per mole of carboxamide reactant.

6. The process defined by claim 1 wherein (b) is an iron chloride, bromide or iodide.

7. A cyclodehydration process for preparing a 2-oxazoline comprising reacting by contacting in liquid phase (a) an N-(2-hydroxyalkyl)- or N-(inertly substituted 2-hydroxyalkyl)carboxamide or a carboxylic acid/amine salt precursor of said carboxamides with (b) a small but catalytic amount of an iron chloride or iron sulfate.

8. The process defined by claim 1 wherein said process is conducted under conditions of temperature and pressure such that the 2-oxazoline product is removed from the reaction mixture as a volatile gas essentially as it is formed.

9. A cyclodehydration process for preparing a 2-oxazoline comprising reacting by contacting in liquid phase (a) an N-(2-hydroxyalkyl)carboxamide or a carboxylic acid/amine salt precursor of a carboxamide corresponding to the formula

wherein R is hydrogen, methyl, ethyl or phenyl and $R_1$-$R_4$ are each hydrogen, with (b) a small but catalytic amount of an iron chloride or sulfate wherein said catalyst is included in amounts of from about 0.005 to about 0.4 mole of iron-containing compound per mole of carboxamide reactant, said reaction being conducted under conditions of temperature and pressure such that the 2-oxazoline product is removed from the reaction mixture as a volatile gas essentially as it is formed.

10. The process defined by claim 1 wherein (a) is an N-(2-hydroxyalkyl)carboxamide.

11. The process defined by claim 10 wherein (a) is an N-(2-hydroxyethyl)carboxamide.

12. The process defined by claim 11 wherein (a) is N-(2-hydroxyethyl)propanamide.

* * * * *

UNITED STATES PATENT AND TRADEMARK OFFICE
CERTIFICATE OF CORRECTION

PATENT NO. : 4,203,900

DATED : May 20, 1980

INVENTOR(S) : Mark E. Kaiser

It is certified that error appears in the above-identified patent and that said Letters Patent are hereby corrected as shown below:

Column 1, line 35, delete "$R^3$" and insert -- $R_3$ --.

Column 1, line 45, delete "2-H2-oxazolins" and insert --2-H-2-oxazolines--.

Column 1, line 50, delete "2-H2-oxazolines" and insert -- 2-H-2-oxazolines --.

Column 2, line 11, delete "2-H2-oxazolines" and insert -- 2-H-2-oxazolines --.

Column 2, line 16, delete "2-H2-oxazolines" and insert -- 2-H-2-oxazolines --.

Column 3, line 44, delete "ae" and insert -- are --.

Column 3, line 46, delete "is" and insert -- in --.

Column 3, line 46, delete "cataytic" and insert -- catalytic --.

UNITED STATES PATENT AND TRADEMARK OFFICE
CERTIFICATE OF CORRECTION

PATENT NO. : 4,203,900
DATED : May 20, 1980
INVENTOR(S) : Mark E. Kaiser

It is certified that error appears in the above-identified patent and that said Letters Patent are hereby corrected as shown below:

Column 3, line 62, delete "cyclodehyration" and insert
-- cyclodehydration --.

Column 4, line 65, delete "2-H-2oxazoline" and insert
-- 2-H-2-oxazoline --.

Column 5, line 54, delete "mole percent" and insert
-- mole percent) --.

Column 6, line 13, delete "N-car-" and insert
-- car- --.

Column 6, line 19, delete "where" and insert -- wherein --.

Signed and Sealed this

Thirtieth Day of September 1980

[SEAL]

Attest:

SIDNEY A. DIAMOND

Attesting Officer

Commissioner of Patents and Trademarks